United States Patent
Dunn et al.

(10) Patent No.: US 6,261,583 B1
(45) Date of Patent: Jul. 17, 2001

(54) MOLDABLE SOLID DELIVERY SYSTEM

(75) Inventors: Richard L. Dunn; Bhagya L. Chandrashekar; Kathleen A. McEnery, all of Fort Collins, CO (US)

(73) Assignee: Atrix Laboratories, Inc., Fort Collins, CO (US)

( * ) Notice: Subject to any disclaimer, the term of this patent is extended or adjusted under 35 U.S.C. 154(b) by 0 days.

(21) Appl. No.: 09/123,723

(22) Filed: Jul. 28, 1998

(51) Int. Cl.$^7$ .......................... A61K 31/765; A61K 9/00
(52) U.S. Cl. ............................. 424/422; 424/426
(58) Field of Search .................... 424/422, 423, 424/426, 487, 78, 489

(56) References Cited

U.S. PATENT DOCUMENTS

| | | |
|---|---|---|
| 3,463,158 | 8/1969 | Schmitt et al. . |
| 3,919,773 | 11/1975 | Freeman . |
| 4,568,536 | 2/1986 | Kronenthal et al. . |
| 4,595,713 | 6/1986 | St. John . |
| 4,650,665 | 3/1987 | Kronenthal et al. . |
| 4,702,917 | * 10/1987 | Schindler .......................... 424/422 |
| 4,722,948 | 2/1988 | Sanderson . |
| 4,774,091 | 9/1988 | Yamahira et al. . |
| 4,800,219 | 1/1989 | Murdoch et al. . |
| 5,149,052 | 9/1992 | Stoy et al. . |
| 5,278,201 | 1/1994 | Dunn et al. . |
| 5,366,734 | 11/1994 | Hutchinson . |
| 5,660,849 | 8/1997 | Polson et al. . |
| 5,681,873 | 10/1997 | Norton et al. . |

FOREIGN PATENT DOCUMENTS

| | | |
|---|---|---|
| 1 135 625 | 11/1982 | (CA) . |
| 1 260 488 | 9/1989 | (CA) . |
| 537559A1 | 10/1991 | (EP) ............................. A61K/9/20 |
| 539751 | 10/1991 | (EP) ............................. A61K/9/00 |
| 0 521 455 A2 | 1/1993 | (EP) . |
| 649662A1 | 4/1995 | (EP) ............................. A61K/31/00 |
| 2 197 658 | 5/1988 | (GB) . |
| 226514 | 2/1990 | (NZ) . |
| 91/01126 | 7/1989 | (WO) ............................. A61K/6/00 |
| 95/27481 | 4/1994 | (WO) ............................. A61K/9/22 |

OTHER PUBLICATIONS

*Kirk–Ottmer's Encyclopedia of Chemical Technology*, Suppl. Vol. 1984.

Leong et al., Bioerodible Polyanhydrides as a Drug Carrier Matrix, *Polymer Preprints*, 25:201–203 (Apr. 1984).

Rosen et al., "Bioerodible polyanhydrides for controlled drug delivery", *Biomaterials*, 4:131–133 (Apr. 1983).

Vert, "Design and Synthesis of Bioresorbable Polymers for the Controlled Release of Drugs", *Polymers in Controlled Drug Deliver*, pp. 117–130 (1987).

Cohn et al., "Biodegradable PEO/PLA block copolymers", *Jour. of Biomed. Materials Research*, 22:993–1009 (1988).

*Encyclopedia of Polymer Science and Engineering*, John Wiley & Sons, Inc., 2:220 (1985).

Higashi et al., "Polymer–hydroxapatite composites for biodegradable bone fillers" , *Biomaterials*, 7:183–187 (May 1986).

Holland et al., "Polymers for Biodegradable Medical Devices. 1. The Potential of Polyesters as Controlled Macromolecular Release Systems", *Journal of Controlled Release*, 4:155–180 (1986).

* cited by examiner

*Primary Examiner*—Thurman K. Page
*Assistant Examiner*—R. Joynes
(74) *Attorney, Agent, or Firm*—Schwegman, Lundberg, Woessner & Kluth, P.A.

(57) ABSTRACT

The invention provides an implant composition for sustained delivery of a biologically active agent. The implant composition includes a biologically active agent, a thermoplastic polymer, an organic liquid and a small amount of an aqueous medium. The thermoplastic polymer is insoluble in water so that the implant composition has the form of a substantially homogeneous pliable, moldable solid.

13 Claims, No Drawings

MOLDABLE SOLID DELIVERY SYSTEM

BACKGROUND OF THE INVENTION

A variety of approaches have been developed for administering a biologically active agent to a patient in a continuous or sustained manner. However, currently available approaches often involve disadvantages or limitations.

In many conventional controlled release systems, the active agents are incorporated into solid, monolithic polymeric matrices. The matrices are hard, unpliable and when surgically implanted into patients' bodies, cannot be molded to conform to the shape of the implant pocket. Often, the sizes and shapes of the matrices and the surgical implantation lead to patient discomfort and complications. In recent years, injectable systems such as polymer solutions and dispersions of microparticles have been developed to overcome these problems. The injectable systems incorporating polymer solutions, however, depend upon the transformation phenomenon associated with the insoluble polymer and aqueous based body fluid. If there is a low quantity of available aqueous fluid at the implant site or the injectable system does not permit substantial influx of water, it does not transform within a reasonable time.

Therefore, development of a surgically implantable solid implant that is moldable and shapable for easy placement and adaptation to the implant site, but then becomes hard and rigid after implantation in the body.

SUMMARY OF THE INVENTION

The invention is directed to an implant composition that exhibits such physical properties as moldability, pliability and extrudability. The invention is also directed to a method of use of the implant composition.

The implant composition is composed of a biocompatible, biodegradable, water-insoluble thermoplastic polymer in combination with a bioactive agent, a biocompatible organic solvent and a small amount of an aqueous medium. The aqueous medium causes the thermoplastic polymers in the implant composition to coagulate at least in part so that the physical form of the implant composition is a pliable, moldable solid.

In use, the implant composition continues its transition to a solidified mass. When implanted at a site infused with body fluid, the composition rapidly continues through this transition to become a fully solidified implant. When little or no body fluid is present at the implant site, the transition to a fully solidified mass occurs at a slower rate. Nevertheless, the integrity of the implant remains because the composition has a pliable, moldable solid nature.

The pliability of the composition can be substantially maintained throughout its life as an implant if a certain subgroup of the organic solvent of the composition is used. Such organic solvent also can act as a plasticizer for the thermoplastic polymer and at least in part may remain in the composition rather than dispersing into body fluid, especially when the organic solvent has low water solubility. According to the invention, this subgroup is termed an organic liquid. An organic liquid having these low water solubility and plasticizing properties may be included in the composition in addition to an organic solvent that is highly water soluble. In the latter situation, the first organic solvent preferably will rapidly disperse into the body fluid.

Because the implant composition of the invention is moldable and pliable, a method of use for the implant composition involves its insertion into a patient by a simple surgical procedure. The moldable, pliable character enables the surgeon to conform the implant composition to the shape of the surgically constructed pocket. Its pliable character also increases the comfort of the patient when it is implanted.

BRIEF DESCRIPTION OF THE DRAWINGS

DETAILED DESCRIPTION OF THE INVENTION

The invention provides a composition and method for controlled release delivery of a biologically active agent. The invention enables effective development of sustained blood and/or tissue levels of agent. The composition includes a thermoplastic polymer which is dispersed or dissolved in an organic solvent, a biologically active agent, an optional organic liquid and a small amount of aqueous medium such as water.

Definitions

The term "moldable" in the context of the present invention means being capable of deforming into, shaping to, or adapting to any three dimensional shape.

The term "pliable" in the context of the present invention means being capable of deforming, bending or flexing under minimal or slight pressure.

The term "flowable" in the context of the present invention means having a viscosity that will permit displacement of a material having this characteristic without application of pressure. A flowable composition is manipulatable, will pass through a small to moderate sized orifice without application of pressure and may be shaped and molded within the tissue defect. Flowable compositions in this context include those having a consistency from that of an emulsion or suspension with a low viscosity or water-like consistency, to that of a high viscosity such as cold molasses.

The term "biocompatible" in the context of the present invention means not causing substantial tissue irritation or necrosis at the implant site.

The term "biodegradable" means degrading over time by the action of enzymes, hydrolytic action and/or other similar mechanisms and "biodegradable" includes the terms bioerodable and bioabsorbable.

The term "bioerodible" means that the implant erodes or degrades at its surfaces over time due, at least in part, to contact with substances found in the surrounding tissue fluids, or by cellular action.

The term "bioabsorbable" means that the resulting implant is broken down and absorbed within the patient's body, for example, by a cell or tissue.

The term "implant site" means a site, in or on which the controlled release formulation is formed or applied, for example, a soft tissue such as muscle or fat, or a hard tissue such as bone. Examples of other implant sites include, but are not limited to, a tissue defect such as a tissue regeneration site; a void space such as a periodontal pocket, a surgical incision or other formed pocket or cavity; a natural cavity such as the oral, vaginal, rectal or nasal cavities, and the cul-de-sac of the eye.

The term "extrudable" in the context of the present invention means that under pressure, a material can be forced as a putty through an orifice.

Implant Composition

The implant composition of the invention includes a biologically active agent in mixture with a moldable, pliable solid formed from a biodegradable, biocompatible, water-insoluble thermoplastic polymer, an organic solvent, an optional organic liquid and a small amount of an aqueous medium.

The implant composition can be prepared by any combination of steps in which the aqueous medium is added to a mixture of the organic solvent and thermoplastic polymer, hereinafter termed "flowable composition", and the biologically active agent is present either in the flowable composition or the aqueous medium. For example, the thermoplastic polymer and organic solvent can first be combined to form the flowable composition as an intermediate. The biologically active agent can be included simultaneously with or subsequent to formation of the flowable composition. The small amount of aqueous medium can then be added slowly to the flowable composition, with stirring or otherwise mixing to form the pliable, moldable implant composition of the invention. A second method involves dissolving the biologically active agent in the aqueous medium and adding it to the flowable composition to solidify the mixture and entrap the active agent.

Biologically Active Agent

According to the invention, a biologically active agent forms part of the implant composition. The biologically active agent is an agent that is capable of providing a local or systemic biological, physiological or therapeutic effect in the body of a patient. The biologically active agent is combined with the other ingredients of the implant composition to form the pliable, moldable solid implant composition. The implant composition possesses a uniform distribution of the ingredients.

The implant composition includes the biologically-active agent in an amount effective to provide the desired level of biological, physiological, pharmacological and/or therapeutic effect in the patient. There is generally no functional upper limit on the amount of the biologically active agent that can be incorporated into the composition. The physical dimensions of the implant size and its ability to provide sustained rather than immediate release of the amount of incorporated biologically active agent, however, limit the incorporated amount of agent. For optimal performance, the concentration of the bioactive agent should not be so high that the implant composition cannot effectively control the rate of release of the bioactive agent. The lower limit of the amount of bioactive agent incorporated into the implant composition depends on the activity of the bioactive material and the period of time desired for treatment. Generally, one skilled in the art of pharmaceutical science can determine the appropriate amount of biologically active agent to incorporate into the implant composition as a function of the physical characteristics of the thermoplastic polymer and organic solvent, the physical characteristics of the biologically active agent and the prescribed treatment regimen for the malcondition of the patient.

Examples of suitable biologically active agents include substances capable of prevention an infection systemically in the animal or locally at the defect site, for example, antibacterial agents such as penicillin, cephalosporins, bacitracin, tetracycline, doxycycline, gentamycin, quinolines, neomycin, clindamycin, kanamycin, and metronidazole; anti-inflammatory agents such as hydrocortisone, and prednisone; antiparasitic agent such as quinacrine, chloroquine, and vidarbine; antifungal agents such as nystatin; antiviral agents such as acyclovir, ribarivin, and interferons; analgesic agents such as salicylic acid, acetaminophen, ibuprofen, naproxen, piroxicam, flurbiprofen, and morphine; local anesthetics such as cocaine, lidocaine, bupivacaine and benzocaine; immunogens (vaccines) for simulating antibodies against hepatitis, influenza, measles, rubella, tetanus, polio, and rabies; peptides such as leuprolide acetate (an LH-RH agonist), nafarelin, and ganirelix.

Substances, or metabolic precursors thereof, which are capable of promoting growth and survival of cells and tissues or augmenting the functioning of cells can also be used, for example, a nerve growth promoting substance, such as a ganglioside or a nerve growth factor; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-$\alpha$), transforming growth factor-$\beta$ (TGF-$\beta$), epidermal growth factor (EGF), fibroblast growth factor (FGF), interleukin-1 (IL-1), and prostaglandins such as $PGE_1$, $PGE_2$ and $PGD_2$; an osteoinductive agent or bone growth promoting substance such a bone chips or demineralized bone material; and antineoplastic agents such as methotrexate, 5-fluouracil, adriamycin, vinblastine, cisplatin, tumor-specific antibodies conjugated to toxins, and tumor necrosis factor.

Other suitable biologically active agents include hormones such as progesterone, testosterone, follicle simulating hormone (FSH) (used for birth control and fertility-enhancement), insulin, and somatotropins; antihistamines such as diphenhydramine and chlorphencramine; cardiovascular agents such as digitalis, nitroglycerine, papaverine and streptokinase; anti-ulcer agents such as cimetidine hydrochloride, and isopropamide iodide; bronchodilators such as metaproternal sulfate and aminophylline; vasodilators such as theophylline, niacin and minoxidil; central nervous system agents such as tranquilizer, b-adrenergic blocking agents, and dopamine; antipsychotic agents such as risperidone and olanzapine; narcotic antagonists such as naltrexone, naloxone and buprenorphine.

Additionally, the implant composition of the invention can be used to deliver genes which encode biologically useful proteins, such as growth hormone, growth hormone releasing factor, pituitary factors, adrenal factors, pancreatic factors, interferon factors, prostaglandin releasing factors and the like.

Additional examples of suitable biologically active agents are provided in U.S. Pat. No. 5,234,529, the disclosure of which is incorporated by reference herein.

Aqueous Medium

The flowable composition used as an intermediate according to this invention will generally undergo a transition to a solid mass when it is contacted with an aqueous medium or body fluid. This transition involves coagulation and/or precipitation of the thermoplastic polymer and dispersion of the organic solvent into the aqueous medium or body fluid. Because of its insolubility in aqueous medium, the thermoplastic polymer usually completely converts to a solid under these circumstances and has the physical characteristics of the polymer alone.

According to the invention, a small amount of aqueous medium, the biologically active agent and the flowable composition are combined to form the implant composition. The implant composition displays such physical characteristics as softness, pliability, easy moldability and extrudability under pressure. Because contact between the flowable composition and an aqueous medium will cause the complete conversion discussed above, it is surprising that addition of a small amount of aqueous medium to the flowable composition yields a material with the forgoing characteristics.

The amount of aqueous medium used is important for this result according to the invention. Typically, the amount of aqueous medium used will range from 5% to 40% by volume relative to the volume of the flowable composition.

Usually, this range of volume means that a few drops of aqueous medium are added to a typical 1 cc volume of flowable composition, the drops being about 0.1 cc in volume and the flowable composition containing about 15% to about 45% by weight thermoplastic polymer relative to the total weight of the flowable composition. As each drop is added and mixed, the texture, viscosity and general physical character of the flowable composition is observed. Sufficient aqueous medium is added when such characteristics as ready pliability, easy moldability and facile extrudability under minimal pressure are observed. Although the biologically active agent can be present in either the aqueous medium or the flowable composition, its contribution to the volume relationship is negligible. Its contribution to any weight percentage is discernible, however, so that the percent by weight discussed in this paragraph is without consideration of the weight of the biologically active agent.

According to the invention, the aqueous medium can be water or any appropriate mixture of pharmaceutically acceptable materials for buffering, stabilizing, complexing, associating, or otherwise forming adjunctive carrier media, isotonic media, nutrient media and the like. Examples include bicarbonate, phosphate, bisulfite buffers, Ficol media, BSA media, EDTA media, antioxidant media, FCS media, saline, physiological buffer solutions and cell-culture media such as agar, bovine media, and any other aqueous based medium optionally containing pharmaceutically acceptable nutrients, minerals, amino acids, lipids, buffers, vitamins and the like. The aqueous medium can also include other components such as emulsifying agents, surfactants, excipients, colorants and the like to stabilize and/or protect the biologically active agent.

Thermoplastic Polymer

According to the invention, the implant composition includes a thermoplastic polymer that will form a sustained release matrix. The thermoplastic polymer is biocompatible and is insoluble in aqueous fluids, such as water or body fluids, and is biodegradable within the body of an animal. Typically, a thermoplastic polymer useful according to the invention will form a pliable, moldable solid when from 5% to about 40% by volume of aqueous medium is added to a solution of the thermoplastic polymer in organic solvent.

The concentration of thermoplastic polymer in the organic solvent can vary depending on the desired viscosity of the implant composition. In applications where the implant composition is to have a moderate viscosity as a moderately thin putty, the viscosity can be appropriately moderated by inclusion of organic liquid, discussed below.

Generally, the concentration of thermoplastic polymer ranges from about 5% to about 95% by weight relative to the total weight of the polymer and organic solvent. Typically, the polymer concentration will range from about 0.1 grams per ml of organic solvent to about 10 grams per ml of organic solvent, preferably from about 0.5 grams to about 3 grams per ml.

Suitable thermoplastic polymers will have hydrolyzable organic functional groups within their polymeric backbones, such as backbones containing amide, ester, urethane, carbonate, phosphoramide, anhydride and/or urea groups. Linear or branched alkylene or arylalkylene groups will be present between those functional groups and functional group side chains may or may not be present. The molecular weight of the thermoplastic polymers useful in the invention will range from about 500 to about 500,000, preferably from about 2,000 to about 200,000, more preferably from about 5,000 to about 100,000.

Examples of suitable thermoplastic polymers are those having formulas incorporating monomeric units such as lactides, glycolides, caprolactones, anhydrides, amides, urethanes, esteramides, orthoesters, dioxanones, acetals, ketals, carbonates, phosphazenes, hydroxybutyrates, hydroxyvalerates, alkylene oxalates, alkylene succinates, and amino acids. The polymeric formulas may incorporate a single monomeric unit or may be copolymers or terpolymers of two or more of these monomeric units, with the monomeric order being random or block. Physical combinations or mixtures these polymers, copolymers and terpolymers may also be employed. Copolymers of any combination of lactide, caprolactone, and glycolide monomeric units are preferred. A random copolymer of lactic acid and glycolic acid are examples.

Organic Solvent

The thermoplastic polymer is combined with a suitable organic solvent to form the basic components of the flowable composition and the implant composition. Suitable organic solvents for use in the present invention are biocompatible and will dissolve the thermoplastic polymer. According to the invention, the organic solvent has a solubility in aqueous medium, ranging from miscible to dispersible (i.e., slightly soluble) and is capable of diffusing into an aqueous medium or into body fluid such as, for example, tissue fluids, such as blood senum, lymph, cerebral spinal fluid (CSF), and saliva.

The solubility or miscibility of the thermoplastic polymer in a particular organic solvent may vary according to factors such as crystallinity, hydrophilicity, capacity for hydrogen bonding, and molecular weight. Consequently, the molecular weight and concentration of the thermoplastic polymer can be adjusted to modify its solubility in the organic solvent. Preferably, the thermoplastic polymer has a low to moderate degree of crystallization, a low to moderate degree of hydrogen bonding, negligible to low solubility in water and high solubility in the organic solvent.

The organic solvent typically contained within the implant composition will have a high water solubility i.e., from those forming a maximum 20% by weight solution in water, to those completely miscible in all respects. An organic solvent with a "high" water solubility diffuses or dissipates from the implant composition into the surrounding aqueous fluids over a period of minutes or hours.

Organic solvents of low water solubility, i.e. those forming aqueous solutions of no more than 5% by weight in water can also be used as the organic solvent of the implant composition. Such organic solvents can also act as plasticizers for the thermoplastic polymer. When the organic solvent has these properties, it is a member of a subgroup of organic solvents termed organic liquids herein. The plasticizer organic liquid influences the pliablity and moldability of the implant composition such that it is rendered more comfortable to the patient when implanted. Moreover, the plasticizer organic liquid has an effect upon the rate of sustained release of the biologically active agent such that the rate can be increased or decreased according to the character of the plasticizer organic liquid incorporated into the implant composition. Although the organic solvent of low water solubility and plasticizing ability can be used alone as the organic solvent of the implant composition, it is preferable to use it in combination as follows. When a high water solubility solvent is chosen for primary use in the implant composition, the plasticizer effect can be achieved by use of a second solvent having a low water solubility and a plasticizing ability. In this instance, the second solvent is a member of the organic liquid subgroup and at least in part will remain in the implant composition for a sustained period. In general, the organic liquid acting as a plasticizer is believed to facilitate molecular movement within the solid thermoplastic matrix. The plasticizing capability enables polymer molecules of the matrix to move relative to each other so that pliability and easy moldability are provided. The plasticizing capability also enables easy movement of the bioactive agent so that in some situations, the rate of sustained release is either positively or negatively affected.

High Water Solubility Organic Solvents

A highly water soluble organic solvent can be generally used in the implant composition and especially when pliability will not be an issue after implantation of the implant composition. Use of the highly water soluble organic solvent will produce an implant having the physical characteristics of and implant made through direct insertion of the flowable composition. Such implants and the precursor flowable compositions are described, for example in U.S. Pat. Nos. 4,938,763 and 5,278,201, the disclosures of which are incorporated herein by reference.

Useful, highly water soluble organic solvents include, for example, substituted heterocyclic compounds such as N-methyl-2-pyrrolidone (NMP) and 2-pyrrolidone; $C_2$ to $C_{10}$ alkanoic acids such as acetic acid and lactic acid, esters of hydroxy acids such as methyl lactate, ethyl lactate, alkyl citrate and the like; monoesters of polycarboxylic acids such as monomethyl succinate acid, monomethyl citric acid and the like; ether alcohols such as glycofurol, glycerol formal, isopropylidene glycol, 2,2-dimethyl-1,3-dioxolone-4-methanol; Solketal; dialkylamides such as dimethylformamide, dimethylacetamide; dimethylsulfoxide (DMSO) and dimethylsulfone; lactones such as ε-caprolactone and butyrolactone; cyclic alkyl amides such as caprolactam; and mixtures and combinations thereof. Preferred solvents include N-methyl-2-pyrrolidone, 2-pyrrolidone, dimethylsulfoxide, ethyl lactate, glycofurol, glycerol formal, and isopropylidene glycol.

Low Water Solubility Organic Solvents

A low water solubility organic solvent may also be used in the implant composition. Preferably, a low water solubility solvent is used when it is desirable to have an implant that remains pliable and is extrudable. Also, the release rate of the biologically active agent can be affected under some circumstances through the use of an organic solvent of low water solubility. Typically such circumstances involve retention of the organic solvent as an organic liquid within the implant product and its function as a plasticizer.

Examples of low water soluble solvents include $C_4$ to $C_{10}$ alkyl alcohols; $C_1$ to $C_6$ alkyl $C_2$ to $C_6$ alkanoates; esters of carbonic acid and alkyl alcohols such as propylene carbonate, ethylene carbonate and dimethyl carbonate, alkyl esters of mono-, di-, and tricarboxylic acids, such as 2-ethyoxyethyl acetate, ethyl acetate, methyl acetate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate; alkyl ketones such as methyl ethyl ketone; as well as other carbonyl, ether, carboxylic ester, amide and hydroxy containing liquid organic compounds having some solubility in water. Propylene carbonate, ethyl acetate, triethyl citrate, isopropyl myristate, and glyceryl triacetate are preferred because of biocompatitibility and pharmaceutical acceptance.

Additionally, mixtures of the foregoing high and low water solubility solvents providing varying degrees of solubility for the matrix forming material can be used to alter the hardening rate of the implant composition. Examples include a combination of N-methyl pyrrolidone and propylene carbonate, which provides a more hydrophobic solvent than N-methyl pyrrolidone alone, and a combination of N-methyl pyrrolidone and polyethylene glycol, which provides a more hydrophilic solvent than N-methyl pyrrolidone alone.

Additives for the Implant Composition

Surfactants and/or emulsifying agents such as sodium dodecylsulfonate or polyvinyl alcohol can be added to the implant composition to improve or stabilize the composition. Other additives include release rate modification agents, such as those discussed in U.S. Pat. No. 5,702,716 which issued from application Ser. No. 07/7767,816, filed Oct. 15, 1991, the disclosures of which are incorporated by reference herein.

Formation of the Implant Composition

The implant composition of the invention is a combination of the biologically active agent, a thermoplastic polymer, an organic solvent and a small amount of aqueous medium. The composition of the invention has the physical form of an homogeneous, pliable, moldable solid. The composition of the invention is administered to a patient needing treatment by usual and typical methods such as by trocar insertion of the implant or by surgical procedure.

The implant composition is formed on site just before it is to be inserted into the patient. The four ingredients can be mixed in an appropriate order that provides homogeneity and the pliable, moldable solid. Preferably, the biologically active agent, the thermoplastic polymer and the organic solvent or organic solvent and organic liquid are mixed together to form the flowable composition with biologically active agent. The portions of each ingredient in the first intermediate are calculated to provide a final concentration of each ingredient in the implant composition that is appropriate for the treatment sought. Next, the aqueous medium can be combined by slow addition of the aqueous medium to the flowable composition with biologically active agent. Preferably, the addition is accomplished by titrating the flowable composition/biologically active agent with small amounts of the aqueous medium, preferably drops, until the desired consistency, pliability and physical form are obtained. Alternatively, the biologically active agent can be combined with the aqueous medium before its mixture with the flowable composition.

The implant composition can be sterilized by radiation, ethylene oxide gas or other non-reactive technique to provide a sterile implant.

Administration of the Implant Composition

The implant composition can be used to administer a sustained amount of a biologically active agent to a patient. When the implant composition is administered, the biologically active agent is entrained in the solid matrix formed by the thermoplastic polymer. As the matrix of the implant degrades over time, and as the diffusion gradient of agent and migrations channels within the matrix cause the agent to migrate, the biologically-active agent is released into adjacent tissue fluids at a controlled rate. The rate at which the biologically-active agent is released from the matrix may be varied, for example, by the solubility of the biologically-active agent in an aqueous medium, the distribution of the agent within the matrix, and the size, shape, porosity, solubility and biodegradability of the matrix.

The implant composition can be administered by any technique known for insertion of implants into body tissue. Preferably, the implant composition is formed just before use and inserted into an incision formed in the patient either under the skin, in the skeletal muscle or through a laproscopic device for insertion of implants into internal organs or tissues. The incision is closed such as by cauterization or suture and the implant composition allowed to remain in situ until the biologically active agent is released completely and the implant matrix is decomposed by the body. Typically, there is no need to remove the implant since it biodegrades within the body. Generally, the medical techniques for implantation of foreign materials into the body are known to skilled surgeons and are practiced following the wisdom and judgment of such medical practitioners.

The present invention is further detailed in the following examples, which are offered by way of illustration and are not intended to limit the invention in any manner. Standard techniques well known in the art or the techniques specifically described below are utilized. All patent cited in the present application are hereby incorporated by reference in their entirety.

EXAMPLES

Example 1

An Implant Composition Prepared with a Thermoplastic Co-Polymer

Poly (DL-lactide-co-glycolide) with an inherent viscosity of 0.2 dL/g and containing carboxyl end groups (PLGH) was dissolved in N-methyl-2-pyrrolidone (NMP) to form a solution with 40% by weight polymer. Approximately 200 ml of the polymer solution was then placed into a glass vial. Distilled water was then dropwise added to the polymer solution while mixing the polymer solution with a stirring rod. After the addition of two drops of water, the addition was stopped and the resulting solution was observed to determine its consistency. Because consistency appeared too fluid, an additional two more drops of water was added. At this point, the polymer solution became thick and turned to a moldable, pliable putty.

Placement of the putty into a buffered aqueous solution caused the putty to become hard.

Example 2

An Implant Composition Prepared with a Thermoplastic Polymer

Poly(DL-lactide)(PLA) with an inherent viscosity of 0.37 dL/g was dissolved in NMP to give a polymer solution with 37% by weight polymer as described in Example 1. The polymer solution was then placed into a glass vial and mixed with a small amount of distilled water added dropwise to the solution. Immediately after addition of approximately 1–2 drops of water, the polymer coagulated and formed a soft, pliable solid implant.

We claim:

1. An implant composition suitable for use as an implant in a patient, comprising: a pliable, moldable solid formed of a uniform distribution of a biocompatible, biodegradable, water-insoluble thermoplastic polymer, a biologically active agent, a biocompatible organic solvent in which the polymer is soluble and an amount of an aqueous medium just sufficient to cause at least some of the thermoplastic polymer to precipitate or coagulate.

2. An implant composition according to claim 1 which is prepared by combining the thermoplastic polymer and organic solvent to form a flowable composition and titrating the flowable composition with the aqueous medium until the flowable composition becomes a soft, pliable moldable solid.

3. An implant composition according to claim 2 wherein the biologically active agent is combined with the organic solvent or with the aqueous medium.

4. An implant composition according to claim 1 wherein the organic solvent is highly water soluble.

5. An implant composition according to claim 1 wherein the organic solvent is a combination of an organic solvent having a high water solubility and an organic solvent having a low water solubility.

6. An implant composition according to claim 1 wherein the organic solvent only partially dissipates into body fluid after the composition has been implanted into body tissue.

7. An implant composition according to claim 1 wherein the thermoplastic polymer has a formula incorporating monomeric units selected from the group consisting of lactides, glycolides, caprolactones, glycerides, anhydrides, amides, urethanes, esteramides, orthoesters, dioxanones, acetals, ketals, carbonates, phosphazenes, hydroxybutyrates, hydroxyvalerates, alkylene oxalates, alkylene succinates, and amino acids and the formula contains the monomeric units random or block order.

8. An implant composition according to claim 7 wherein the thermoplastic polymer is a copolymer of two or more lactide, caprolactone, or glycolide monomeric units.

9. An implant composition according to claim 1 wherein the amount of aqueous medium ranges from 5 to 40% by volume relative to the volume of a flowable composition of the thermoplastic polymer and the organic solvent.

10. A method of administering a sustained release dose of a biologically active agent to a patient comprising administering to the patient an effective amount of an implant composition according to claim 1.

11. A method according to claim 10 wherein the implant is inserted into the patient.

12. An implant according to claim 1 wherein the organic solvent is dispersible in water.

13. An implant according to claim 1 wherein the organic solvent is capable of dispersing into body fluid when placed in body tissue.

* * * * *

UNITED STATES PATENT AND TRADEMARK OFFICE
CERTIFICATE OF CORRECTION

PATENT NO. : 6,261,583 B1  
DATED : July 17, 2001  
INVENTOR(S) : Richard L. Dunn, Bhagya L. Chandrashekar and Kathleen A. McEnery It is certified that error appears in the above-identified patent and that said Letters Patent is hereby corrected as shown below:

Column 1,  
Line 28, insert -- is needed -- after "body".

Column 6,  
Line 9, insert -- of -- after "mixtures".

Column 8,  
Line 11, delete "07/7767,816" and insert -- 07/767,816 -- therefor.  
Lines 29 and 35, insert -- a -- between "with" and "biologically".

Column 9,  
Line 13, delete "patent" and insert -- patents --, therefor.

Signed and Sealed this

First Day of April, 2003

JAMES E. ROGAN  
*Director of the United States Patent and Trademark Office*